US00PP13176P2

(12) United States Plant Patent
Brown

(10) Patent No.: US PP13,176 P2
(45) Date of Patent: Nov. 5, 2002

(54) DIASCIA PLANT NAMED 'CODIARED'

(75) Inventor: Graham Brown, Baulkham Hills (AU)

(73) Assignee: Nuflora International Pty. Ltd., Sydney (AU)

( * ) Notice: Subject to any disclaimer, the term of this patent is extended or adjusted under 35 U.S.C. 154(b) by 0 days.

(21) Appl. No.: 09/996,216

(22) Filed: Nov. 30, 2001

(51) Int. Cl.[7] ..... A01H 5/00

(52) U.S. Cl. ..... Plt./263

(58) Field of Search ..... Plt./263

*Primary Examiner*—Bruce R. Campell
*Assistant Examiner*—Anne Marie Grünberg
(74) *Attorney, Agent, or Firm*—C. A. Whealy

(57) ABSTRACT

A new and distinct cultivar of Diascia plant named 'Codiared', characterized by its upright, somewhat outwardly spreading, and compact plant habit; freely and continuous branching; and numerous red purple-colored flowers.

1 Drawing Sheet

BOTANICAL CLASSIFICATION/CULTIVAR DESIGNATION

*Diascia×hybrida* cultivar Codiared.

BACKGROUND OF THE INVENTION

The present Invention relates to a new and distinct cultivar of Diascia plant, botanically known as *Diascia×hybrida*, and hereinafter referred to by the cultivar name Codiared.

The new Diascia is a product of a planned breeding program conducted by the Inventor in Cobbitty, New South Wales, Australia. The objective of the breeding program is to create new compact Diascias with numerous uniquely-colored flowers.

The new Diascia orignated from a cross made by the Inventor in 1998 of a proprietary *Diascia×hybrida* selection identified as X96.13.2, not patented, as the female, or seed parent, with an unidentified proprietary selection of *Diascia ringens*, not patented, as the male, or pollen parent. The new Diascia was selected as a single plant from the resulting progeny by the inventor in 1998, in Cobbitty, New South Wales, Australia, on the basis of its numerous red purple-colored flowers.

Asexual reproduction of the new cultivar by terminal cuttings taken in Cobbitty, New South Wales, Australia since 1998 has shown that the unique features of this new Diascia are stable and reproduced true to type in successive generations.

SUMMARY OF THE INVENTION

Plants of the cultivar Codiared have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Codiared'. These characteristics in combination distinguish 'Codiared' as a new and distinct cultivar:

1. Upright, somewhat outwardly spreading and compact plant habit.
2. Freely and continuous branching.
3. Numerous red purple-colored flowers.

Compared to plants of the female parent, the selection X96.13.2, plants of the new Diascia are more compact in plant habit. In addition plants of the new Diascia and the female parent differ in flower color as plants of the selection X96.13.2 have light red-colored flowers.

Compared to plants of the male parent, the unidentified proprietary selection of *Diascia ringens*, plants of the new Diascia flower earlier. In addition plants of the new Diascia and the male parent differ in flower color as plants of the unidentified proprietary selection of *Diascia ringens* have pink-colored flowers.

Plants of the new Diascia can be compared to plants of the Diascia cultivar Herace, disclosed in U.S. Plant patent applicaton Ser. No. 09/639,898 (abandoned). In side-by-side comparisons conducted in Cobbitty, New South Wales, Australia, plants of the new Diascia were more compact and had larger flowers than plants of the cultivar Herace.

Plants of the new Diascia can also be compared to plants of the cultivar Strawberry Sundae, disclosed in U.S. Plant Pat. No. 11,488. In side-by-side comparisons conducted in Encinitas, Calif., plants of the new Diascia differed from plants of the cultivar Strawberry Sundae in the following characteristics:

1. Plants of the new Diascia were shorter and more compact than plants of the cultivar Strawberry Sundae.
2. Plants of the new Diascia had smaller and flatter flowers than plants of the cultivar Strawberry Sundae.
3. Plants of the new Diascia had red purple-colored flowers whereas plants of the cultivar Strawberry Sundae had bright pink-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new Diascia.

The photograph at the top of the sheet comprises a side perspective view of three typical flowering plants of 'Codiared' grown in a 20-cm container.

The photograph at the bottom of the sheet comprises a close-up view of typical leaves, flowering stems, flower buds, developing flowers, and fully opened flowers of 'Codiared'.

DETAILED BOTANICAL DESCRIPTION

The aforementioned photographs and following observations and measurements describe plants grown in Encinitas, Calif., in an outdoor nursery under full sunlight conditions during the late winter and early spring with day temperatures averaging 18° C. and night temperatures averaging 13° C. Plants were grown for 14 weeks in 20-cm containers with three plants per container and were pinched two times. Color references are made to The Royal Horitcultural Society Colour Chart, version 1995, except where general terms of ordinary dictionary significance are used.

Botanical classification: *Diascia×hybrida* cultivar Codiared.

Parentage:

*Female parent.*—Proprietary *Diascia×hybrida* selection identified as X96.13.2, not patented.

*Male parent.*—Unidentified proprietary selection of *Diascia ringens*, not patented.

Propagation:

*Type cutting.*—Terminal vegetative cuttings.

*Time to initiate roots.*—Summer: About 10 days at 20° C., Winter: About 12 days at 10° C.

*Time to develop roots.*—Summer: About 26 days at 20° C. Winter: About 28 days at 10° C.

*Root description.*—Fine and fibrous.

*Rooting habit.*—Freely branching.

Plant description:

*Form.*—Upright, somewhat outwardly spreading and compact plant habit. Freely branching with lateral branches potentially forming at every node. Moderately vigorous growth habit.

*Plant height.*—About 23 cm.

*Plant diameter.*—About 24 cm.

*Lateral branches.*—Length: About 21 cm. Diameter: About 2 mm. Internode length: About 1.8 to 3 cm. Texture: Smooth, glabrous. Color: 146B.

*Foliage description.*—Arrangement: Opposite; simple. Quantity per lateral branch: About 20. Length: About 2 cm. Width: About 1.4 cm. Shape: Deltoid. Apex: Acute. Base: Truncate, rounded. Margin: Slightly serrate. Texture: Smooth, glabrous. Venation pattern: Palmate. Color: Young and mature foliage, upper sufrace: 147A. Young and mature foliage, lower surface: 147B. Venation, upper surface: 147A. Venation, lower surface: 147B. Petiole length: About 3 mm. Petiole diameter: About 2 mm. Petiole color: 147B.

Flower description:

*Flower type and habit.*—Solitary axillary flowers: zygomorphic. Five modified petals fused at base: two upper (banner) petals, two lateral petals and one larger lower lip petal. Flowers not persistent. Very freely flowering; typically about 14 buds and flowers per lateral branch. Flowers face mostly outward.

*Natural flowering season.*—Plants typically flower from March through June in the Northern Hemisphere; flowering continuous during this period.

*Flower longevity on the plant.*—About 3 to 4 days.

*Fragrance.*—Not detected.

*Flower size.*—Height: About 2 cm. Width: About 1.7 cm. Depth (height): About 1 cm.

*Flower buds* (*showing color*).—Length: About 5.5 mm. Diameter: About 5.5 mm. Shape: Oval. Color: 78B to 78C.

*Petals.*—Quantity/arrangement: Five modified petals fused at base: two upper (banner) petals, two lateral petals and one larger lower lip petal. Base of banner petals with indented yellow eyespots; lower surfaces of lateral petals modified into nectar spurs; and lower lip petal convex forming horizontal insect landing platform. Length: Banner petals: About 5 mm. Lateral petals: About 7 mm. Lower lip petal: About 1.2 cm. Width: Banner petals: About 8 mm. Lateral petals: About 5 mm. Lower tip petal: About 1 cm. Lateral petal spur: Length: About 1 cm. Diameter, at petal attachment: About 2 mm. Shape, all petals: Roughly spatulate. Apex, all petals: Rounded. Margin, all petals: Entire. Texture, all petals: Smooth, velvety. Color, all petals: Upper surface, when opening: 71B. Lower surface, when opening: 77A to 77B. Upper surface, fully opened: 63A; at base of petals, 77A; main color fading to 78C to 78D with subsequent development. Lower surface, fully opened: 63B. Nectar spurs: 78C. Eyespot on banner petals: 5A.

*Sepals*—Arrangement/appearance: Single whorl of five sepals fused at base; star-shaped. Calyx length: About 3 mm. Calyx diameter: About 5 mm. Shape: Elliptic. Apex: Acute. Margin: Entire. Texture, upper and lower surfaces: Smooth, glabrous. Color: Upper surface: 146B. Lower surface: 146A.

*Peduncles.*—Length: About 1 cm. Width: Less than 1 mm. Angle: About 45° from the stem. Strength: Moderately strong; slender. Texture: Smooth. Color: 144B.

*Reproductive organs.*—Stamens: Quantity per flower: Four. Anther shape: Ovoid. Anther length: Less than 1 mm. Anther color: 7A. Pollen amount: Scarce. Pollen color: 7A. Pistils: Quantity per flower: One. Pistil length: About 2.5 mm. Style length: About 1 mm. Style color: 149A. Stigma shape: Rounded. Stigma color: 149A. Ovary color: 144B.

*Seed/fruit.*—Seed nor fruit production has not been observed.

Disease/pest resistance: Plants of the new Diascia have not been noted to be resistant to pathogens or pests common to Diascia.

Temperature tolerance: Plants of the new Diascia have been observed to tolerate temperatures from 0 to 32° C.

It is claimed:

1. A new and distinct cultivar of Diascia plant named 'Codiared', as illustrated and described.

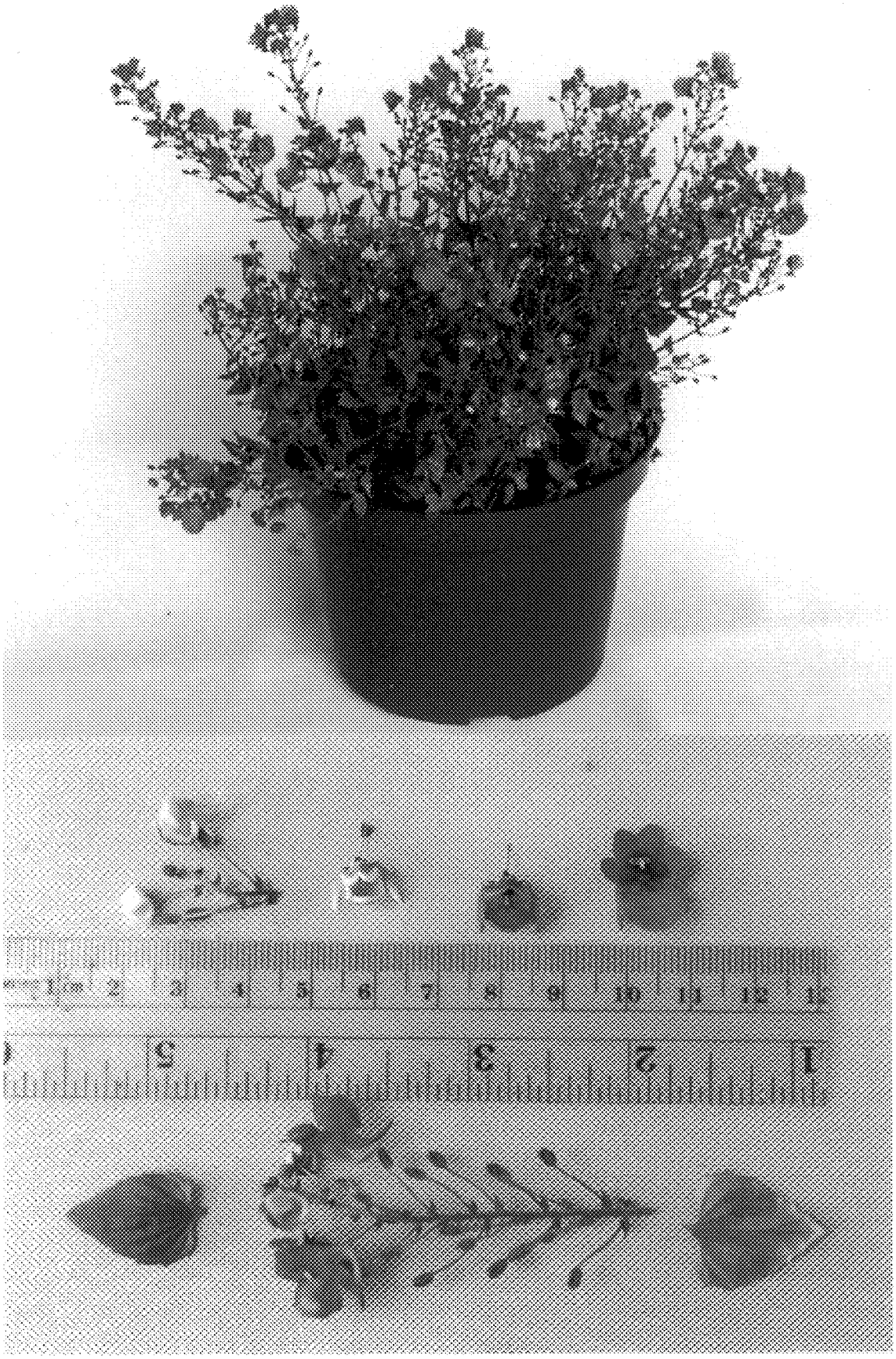

* * * * *